US011105765B2

(12) United States Patent
Yuan et al.

(10) Patent No.: US 11,105,765 B2
(45) Date of Patent: Aug. 31, 2021

(54) BIOSENSOR DEVICE AND METHOD FOR MANUFACTURING THEREOF AND METHOD FOR DETECTING BIOLOGICAL MOLECULES

(71) Applicant: NEAT BIOTECH, INC., Hsinchu (TW)

(72) Inventors: Chiun-Jye Yuan, Hsinchu (TW); Chun-Lung Lien, Hsinchu County (TW); Paul C.-P. Chao, Taipei (TW)

(73) Assignee: NEAT BIOTECH, INC., Hsinchu (TW)

( * ) Notice: Subject to any disclaimer, the term of this patent is extended or adjusted under 35 U.S.C. 154(b) by 0 days.

(21) Appl. No.: 15/788,821

(22) Filed: Oct. 20, 2017

(65) Prior Publication Data

US 2019/0004002 A1 Jan. 3, 2019

(30) Foreign Application Priority Data

Jun. 29, 2017 (TW) .................................. 106121830

(51) Int. Cl.
*G01N 27/327* (2006.01)
*G01N 33/553* (2006.01)
(Continued)

(52) U.S. Cl.
CPC ....... *G01N 27/3275* (2013.01); *C12Q 1/6816* (2013.01); *C12Q 1/6825* (2013.01);
(Continued)

(58) Field of Classification Search
CPC .. C25B 11/00; G01N 27/403; G01N 27/3275; G01N 33/553; G01N 33/5438;
(Continued)

(56) References Cited

U.S. PATENT DOCUMENTS 6,110,354 A * 8/2000 Saban ................... G01N 27/27
204/412
6,740,518 B1 * 5/2004 Duong ............... G01N 27/3277
435/287.2
(Continued)

FOREIGN PATENT DOCUMENTS

CN 102830161 A 12/2012
CN 104737007 A 6/2015
(Continued)

OTHER PUBLICATIONS

Napat Triroj et al., "Microfluidic chip-based nanoelectrode array as miniaturized biochemical sensing platform for prostate-specific antigen detection," Biosensors and Bioelectronics, vol. 26, 2011, pp. 2927-2933.
(Continued)

*Primary Examiner* — Gurpreet Kaur
(74) *Attorney, Agent, or Firm* — McClure, Qualey & Rodack, LLP

(57) ABSTRACT

A biosensor device includes a substrate plate, a metal conductive layer, a plurality of working electrodes and an insulating layer. The metal conductive layer is disposed over the substrate plate and has an upper surface. The working electrodes are disposed over the upper surface of the metal conductive layer, wherein each of the working electrodes has a top surface and each of the top surfaces is higher than the upper surface of the metal conductive layer. The insulating layer covers the metal conductive layer and surrounds the working electrodes, wherein an upper surface of the insulating layer is located between the top surfaces and the upper surface of the metal conductive layer such that the working electrodes protrude beyond the upper surface of the insulating layer. A method for manufacturing the biosensor
(Continued)

device and a method for detecting biological molecules by using the biosensor device are also provided herein.

14 Claims, 9 Drawing Sheets

(51) Int. Cl.
*G01N 33/543* (2006.01)
*C12Q 1/68* (2018.01)
*H01L 21/283* (2006.01)
*H01L 21/3213* (2006.01)
*H01L 21/285* (2006.01)
*C12Q 1/6825* (2018.01)
*H01L 21/311* (2006.01)
*C12Q 1/6834* (2018.01)
*H01L 21/3105* (2006.01)
*C12Q 1/6816* (2018.01)

(52) U.S. Cl.
CPC ....... *C12Q 1/6834* (2013.01); *G01N 33/5438* (2013.01); *G01N 33/553* (2013.01); *H01L 21/28506* (2013.01); *H01L 21/31053* (2013.01); *H01L 21/31111* (2013.01); *H01L 21/32133* (2013.01); *H01L 21/32139* (2013.01)

(58) Field of Classification Search
CPC ......... H01L 21/28506; H01L 21/32133; H01L 21/32139; H01L 21/31053; H01L 21/31111; C01B 31/02; B82Y 30/00; B82Y 40/00; B32B 7/02; Y10S 977/84
See application file for complete search history.

(56) References Cited

U.S. PATENT DOCUMENTS

| | | | |
|---|---|---|---|
| 6,741,518 B2 | 5/2004 | Kojima et al. | |
| 7,625,469 B1 | 12/2009 | Yelton et al. | |
| 7,635,420 B1* | 12/2009 | Li | B03C 5/026 204/547 |
| 2004/0045839 A1 | 3/2004 | Thewes et al. | |
| 2004/0106203 A1 | 6/2004 | Stasiak et al. | |
| 2004/0248282 A1 | 12/2004 | Sobha M. et al. | |
| 2007/0068242 A1* | 3/2007 | DiFoggio | E21B 47/102 73/152.55 |
| 2007/0210349 A1 | 9/2007 | Lu et al. | |
| 2008/0093662 A1* | 4/2008 | Park | G11C 16/0408 257/324 |
| 2009/0045061 A1 | 2/2009 | Farrow et al. | |
| 2010/0006451 A1* | 1/2010 | Gordon | G01N 33/5438 205/777.5 |
| 2013/0029872 A1* | 1/2013 | Ishige | G01N 27/3275 506/9 |
| 2014/0087375 A1 | 3/2014 | Kelley et al. | |
| 2015/0011421 A1* | 1/2015 | Li | G01N 27/27 506/11 |
| 2015/0139856 A1* | 5/2015 | Yamada | G01N 21/658 422/69 |
| 2016/0072087 A1 | 3/2016 | Ferro et al. | |
| 2017/0226557 A1* | 8/2017 | Wang | C12Q 1/005 |
| 2018/0020957 A1 | 1/2018 | Kinser | |

FOREIGN PATENT DOCUMENTS

| | | |
|---|---|---|
| JP | 2001242135 A | 9/2001 |
| JP | 2005114427 A | 4/2005 |
| JP | 2006337273 A | 12/2006 |
| JP | 2013160557 A | 8/2013 |
| TW | M411436 U1 | 9/2011 |
| TW | 201416437 A | 5/2014 |
| TW | 201435340 A | 9/2014 |
| TW | 201508271 A | 3/2015 |
| WO | 2015184465 A1 | 12/2015 |

OTHER PUBLICATIONS

Adaikkappan Periyakaruppan et al., "Label-Free Detection of Cardiac Troponin-I Using Carbon Nanofiber Based Nanoelectrode Arrays", Analytical Chemistry, Feb. 5, 2013, pp. 3858-3863.

* cited by examiner

200

200

BIOSENSOR DEVICE AND METHOD FOR MANUFACTURING THEREOF AND METHOD FOR DETECTING BIOLOGICAL MOLECULES

RELATED APPLICATIONS

This application claims priority to Taiwan Application Serial Number 106121830, filed Jun. 29, 2017, which is herein incorporated by reference.

BACKGROUND

Field of Invention

The present invention relates to a biosensor device and method for manufacturing thereof, and a method for detecting biological molecules by using the biosensor device.

Description of Related Art

Recently, a variety of detection methods for biological molecules have been developed to diagnose various diseases, conduct researches associated with physiology, metabolism and monitor environmental factors, etc. The development of Micro-electromechanical Systems (MEMS) have attracted much attention due to its integration of semiconductor processes and precision machinery technologies, which can be used to manufacture a semiconductor microchip for sensing optics, chemicals, biological molecules or others properties. However, as the semiconductor industry has progress into nanometer technology nodes in pursuit of higher device density, higher performance and lower costs, challenges from manufacturing and design issues have resulted in the development in three-dimensional design. Accordingly, there is an urgent need for developing biosensor chips with higher performance and low costs.

SUMMARY

An aspect of the present disclosure provides a method for manufacturing a biosensor device, including the step of: providing a substrate plate; forming a metal conductive layer over the substrate plate, and the metal conductive layer having an upper surface; forming a plurality of working electrodes over the upper surface of the metal conductive layer, wherein each of the working electrodes has a top surface that is higher than the upper surface of the metal conductive layer; and forming an insulating layer covering the metal conductive layer and surrounding the working electrodes, wherein an upper surface of the insulating layer is between the top surfaces and the upper surface of the metal conductive layer so that the working electrodes protrudes beyond the upper surface of the insulating layer.

According to some embodiments of the present disclosure, the step of forming the working electrodes includes: depositing an electrically conductive layer over the upper surface of the metal conductive layer; and patterning the electrically conductive layer to form the working electrodes.

According to some embodiments of the present disclosure, each of the working electrodes has a first height ranged from about 0.05 μm to about 0.6 μm.

According to some embodiments of the present disclosure, each of the working electrodes has an aspect ratio ranged from about 0.125 to about 7.5.

According to some embodiments of the present disclosure, the step of forming the insulating layer includes: depositing an insulating material layer over the metal conductive layer and the working electrodes; performing a planarization process on the insulating material layer to form a planarized insulating material layer; and etching the planarized insulating material layer to form the insulating layer.

According to some embodiments of the present disclosure, each of the working electrodes further includes a sidewall adjoining the top surface, and the insulating layer covers a portion of each of the sidewalls.

According to some embodiments of the present disclosure, each of the working electrodes protrudes from the upper surface a second height, and the second height is about 0.01 μm to about 0.5 μm.

According to some embodiments of the present disclosure, the working electrodes are in a shape of a cylinder, a triangular prism, a quadrangular prism, a pentagonal prism, a hexagonal prism or an octagonal prism.

According to some embodiments of the present disclosure, the method further includes connecting a plurality of biological probes to the working electrodes, wherein the biological probes are nucleic acid, cell, antibody, enzyme, polypeptide or combinations thereof.

An aspect of the present disclosure provides a biosensor device, including: a substrate plate; a metal conductive layer disposed over the substrate plate and the metal conductive layer having an upper surface; a plurality of working electrodes disposed over the upper surface of the metal conductive layer, wherein each of the working electrodes has a top surface that is higher than the upper surface of the metal conductive layer; and an insulating layer covering the metal conductive layer and surrounding the working electrodes, wherein an upper surface of the insulating layer is between the top surfaces and the upper surface of the metal conductive layer, so that the working electrodes protrudes beyond the upper surface of the insulating layer.

According to some embodiments of the present disclosure, each of the working electrodes has a first height ranged from about 0.05 μm to about 0.6 μm.

According to some embodiments of the present disclosure, each of the working electrodes has an aspect ratio ranged from about 0.125 to about 7.5.

According to some embodiments of the present disclosure, the metal conductive layer further includes a sidewall adjoining the upper surface of the metal conductive layer, and the insulating layer covers the sidewall of the metal conductive layer.

According to some embodiments of the present disclosure, each of the working electrodes further includes a sidewall adjoining the top surface, and the insulating layer covers a portion of each of the sidewalls.

According to some embodiments of the present disclosure, each of the working electrodes protrudes from the upper surface a second height, and the second height is about 0.01 μm to about 0.5 μm.

According to some embodiments of the present disclosure, the working electrodes are in a shape of a cylinder, a triangular prism, a quadrangular prism, a pentagonal prism, a hexagonal prism or an octagonal prism.

According to some embodiments of the present disclosure, the biosensor device further includes a plurality of biological probes connected to the working electrodes, wherein the biological probes are nucleic acid, cell, antibody, enzyme, polypeptide or combinations thereof.

Another aspect of the present disclosure provides a method for detecting biological molecules, including: providing a sample comprising a target molecule; providing the biosensor device of claim 10; connecting a plurality of biological probes to the working electrodes; applying a voltage to the working electrodes such that the working electrodes generate an electric field surrounding the working electrodes; and contacting the sample with the biological probes such that the target molecule in the sample is bound to the biological probes, thereby generating a signal from the working electrodes.

According to some embodiments of the present disclosure, the step of applying the voltage to the working electrodes includes: applying a voltage to the working electrodes such that 75% of the maximal electric field intensity occurs at about 27% to about 40% of the second height from the top surfaces toward the upper surface of the insulating layer.

According to some embodiments of the present disclosure, the step of applying the voltage to the working electrodes includes: applying a voltage to the working electrodes such that 50% of the maximal electric field intensity occurs at about 80% to about 93% of the second height from the top surfaces toward the upper surface of the insulating layer.

BRIEF DESCRIPTION OF THE DRAWINGS

The present disclosure can be more fully understood by reading the following detailed description of the embodiment when read with the accompanying figures.

DETAILED DESCRIPTION

Figure 1:
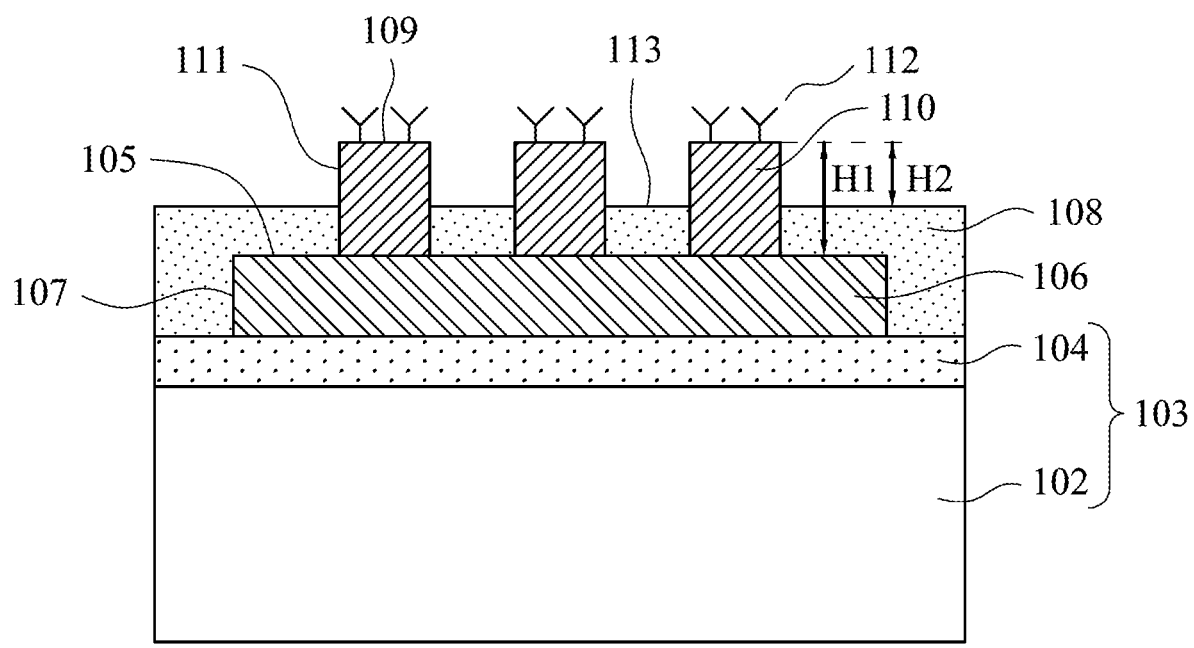
FIG. 1 is a cross-sectional view of a biosensor device according to some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature "over" or "on" a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof.

FIG. 1 is a cross-sectional view of a biosensor device in accordance with some embodiments. As shown in FIG. 1, the biosensor device 100 includes a substrate plate 103, a metal conductive layer 106, a second insulating layer 108, a plurality of working electrodes 110 and a plurality of biological probes 112. In some embodiments, the substrate plate 103 includes a base substrate 102 and a first insulating layer 104. The substrate plate 103 may further include, but not limited to, GaN, SiC, SiGe, Ge, or combinations thereof, or other semiconductor materials. The base substrate 102, for example, may be a silicon substrate. The base substrate 102 may include various doping configurations, depending on design requirements as known in the art. In one embodiment, the base substrate 102 may be a highly-doped and low-resistivity semiconductor substrate. In another embodiment, the substrate plate 103 is a glass substrate without the first insulating layer 104.

The first insulating layer 104 is disposed over the base substrate 102. In one embodiment, the first insulating layer 104 may include, but not limited to, an oxide, a nitride, an oxynitride or combinations thereof, such silicon oxide, silicon nitride, and silicon oxynitride. The first insulating layer 104 is formed of low-k dielectric material such that the biosensor device 100 has excellent insulating properties. In some embodiments, the first insulating layer 104 may have a thickness in a range from about 0.02 μm to about 0.25 μm, for example, about 0.10 μm, about 0.15 μm or about 0.20 μm.

The metal conductive layer 106 is disposed over the substrate plate 103, and has a sidewall 107 and upper surface 105. The sidewall 107 adjoins the upper surface 105 and the second insulating layer 108 covers the sidewall 107. In one embodiment, the metal conductive layer 106 may include, but not limited to, Ti, Ni, Ag, Al, Al/Cu alloy, Al/Si/Cu alloy or combinations thereof. In one embodiment, the metal conductive layer 106 may have a thickness in a range from about 0.02 μm to about 0.7 μm, for example, about 0.1 μm, about 0.2 μm, about 0.3 μm, about 0.4 μm, about 0.5 μm or about 0.6 μm.

Each working electrode 110 is disposed over the upper surface 105 of the metal conductive layer 106, and has a top surface 109 and a sidewall 111. Each top surface 109 is higher than the upper surface 105 of the metal conductive layer 106, each sidewall 111 adjoins each top surface 109, and the second insulating layer 108 merely covers a portion of each sidewall 111. Each working electrode 110 has a first height H1 protruding beyond the metal conductive layer 106. In one embodiment, each working electrode 110 may have the first height H1 in a range from about 0.05 μm to about 0.6 μm, for example, about 0.05 μm, about 0.1 μm, about 0.2 μm, about 0.3 μm or about 0.4 μm. In some embodiments, each working electrode 110 may have a width of about 0.08 μm to about 0.4 μm, for example, about 0.08 μm, about 0.1 μm, about 0.2 μm or about 0.3 μm. In one embodiment, each working electrode 110 may have an aspect ratio in a range from about 0.125 to about 7.5, for example, about 0.2 or about 0.3.

In some embodiments of the present disclosure, the working electrodes 110 may be in a shape of a cylinder, a triangular prism, a quadrangular prism, a pentagonal prism, a hexagonal prism or an octagonal prism. In some embodiments, the working electrodes 110 may include, but not limited to, Ta, TaN, Cu, Ti, TiN, W, Ti, Ni, Ag, Al, Al/Cu alloy, Al/Si/Cu alloy or combinations thereof. In some embodiments, the material of the working electrodes 110 may be TiN, preferably.

The biological probes 112 may be modified and connected to the working electrodes 110 using various methods known in the art. In accordance with some embodiments of the present disclosure, the biological probes 112 may include, but not limited to, nucleic acid, cell, antibody, enzyme or combinations thereof. It is noted that the biological probes 112 may detect various biological molecules. For example, when using antibody as the biological probe 112, a target molecule (i.e., antigen) in a sample may be bound or reacted with the biological probe 112, thereby detecting the presence of the target molecule using various techniques known in the art.

The second insulating layer 108 covers the metal conductive layer 106 and surrounds the working electrodes 110. The upper surface 113 of the second insulating layer 108 is positioned between the top surfaces 109 of the working electrodes 110 and the upper surfaces 105 of the metal conductive layer 106 such that the working electrodes 110 protrudes beyond the upper surface 113 of the second insulating layer 108. The protruding portion has a second height H2, which is the vertical distance from each top surface 109 to the upper surface 113 of the second insulating layer 108. In some embodiments, the second height H2 may be in a range from about 0.01 μm to about 0.5 μm, for example, about 0.05 μm, about 0.15 μm, about 0.3 μm or about 0.45 μm. Therefore, when a voltage is applied to the working electrodes 110, the working electrodes 110 generate an electric field surrounding the protruding working electrodes 110. The coverage of the electric field is not limited to the top surfaces 109 of the working electrodes 110 and further extends to the sidewalls 111 of the working electrodes 110 so that the electrochemical reaction is greatly enhanced, thereby increasing the strength of signal. At the same applied voltage, the working electrode 110 having three-dimensional structure provides superior sensitivity over the planar working electrode of the prior art.

In some embodiments, the second insulating layer 108 may include, but not limited to, an oxide, a nitride, an oxynitride or combinations thereof, such as silicon oxide, silicon nitride, and silicon oxynitride. In some embodiments, the material of the first insulating layer 104 is the same as the material of the second insulating layer 108. In yet some embodiments, the material of the first insulating layer 104 is different from the material of the second insulating layer 108.

In addition, when a voltage is applied to the working electrodes 110, background signal is also generated, and that interferes the detection result. The generation of the background signal is related to the cross-sectional area of electrode. When the cross-sectional area (CA) is larger, the background signal is higher. In accordance with some embodiments of the present disclosure, when the voltage is applied to the working electrodes 110, the working electrodes 110 generate the electric field having a coverage range that is larger than the planar working electrodes of the prior art. The coverage range of the electric field is not limited to the top surfaces 109 of the working electrodes 110 and further extends to the sidewalls 111 of the working electrodes 110. Accordingly, the widths of the working electrodes 110 can be adjusted to be smaller than that of the planar working electrodes in the prior art while sustaining the same effective coverage of the electric field. Therefore, in accordance with embodiments of the present disclosure, the widths of the working electrodes 110 may be smaller than the widths of the planar working electrodes in the prior art, and have smaller cross-sectional area than the planar working electrodes of the prior art, thereby reducing the generation of the background signal.

As described above, in some embodiments, the first height H1 of each working electrode 110 is ranged from about 0.05 μm to about 0.6 μm. When the first height H1 of each working electrode 110 is less than 0.05 μm, the second height H2 of each protruding portion of working electrode 110 may be less than 0.01 μm. In this situation, when the voltage is applied to the working electrodes 110, the extension of the coverage of the effective electric field is limited and thus the enhancement of the electrochemical reaction of the biological probe 112 is unobvious. Accordingly, it can be seen that the higher the protruding portion of the working electrodes 110, the wider the effective electric field coverage is and the better the electrochemical reaction is. It is noted that each working electrode 110 has an aspect ratio ranged from about 0.125 to about 7.5. When each working electrode 110 has the aspect ratio greater than 7.5, the working electrodes are easily formed with defects in structure, thereby reducing the reliability of entire device.

Figure 2:
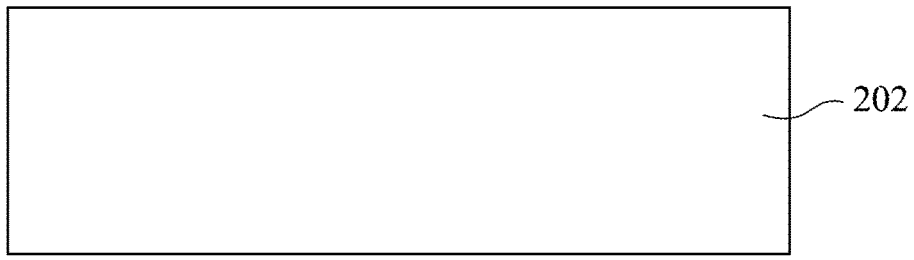
FIGS. 2-12 are cross-sectional views of a biosensor device during various stages of production according to some embodiments of the present disclosure.
Figure 3:
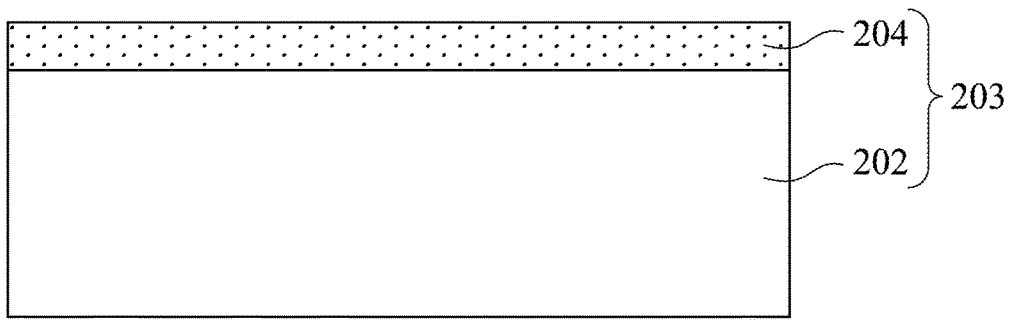

FIGS. 2-12 are cross-sectional views of a biosensor device during various stages of production in accordance with some embodiments of the present disclosure. As shown in FIG. 2 and FIG. 3, a substrate plate 203 is provided. In some embodiments, the substrate plate 203 includes a base substrate 202 and a first insulating layer 204 formed over the base substrate 202. The first insulating layer 204 may be formed using atomic layer deposition (ALD), physical vapor deposition (PVD), chemical vapor deposition (CVD), chemical oxidation, heat oxidation and/or other suitable process. In one embodiment, the first insulating layer 204 may include, but not limited to, an oxide, a nitride, an oxynitride or combinations thereof, such as silicon oxide, silicon nitride, and silicon oxynitride. In some embodiments, the first insulating layer 204 is formed with a thickness ranged from about 0.02 μm to about 0.25 μm, for example, about 0.10 μm, about 0.15 μm or about 0.20 μm.

Figure 4:
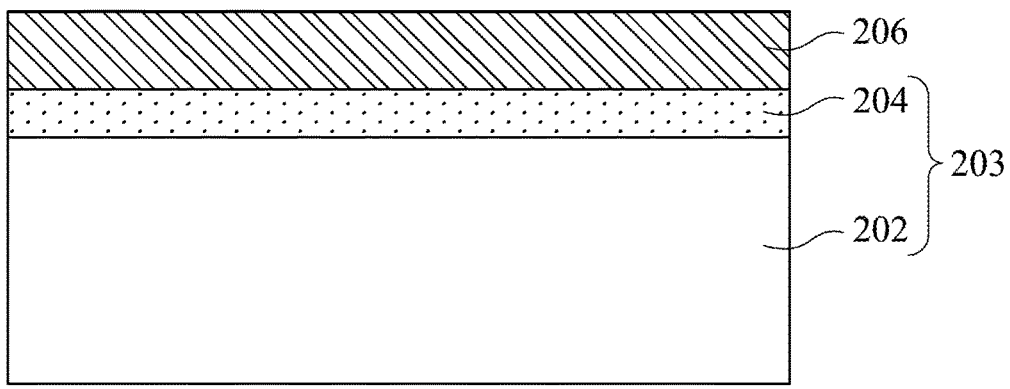

Referring to FIG. 4, in this step, a metal conductive layer 206 is formed over the first insulating layer 204. In some embodiments, the metal conductive layer 206 may be formed using PVD, CVD, electron beam evaporation, sputtering, electroplating and/or other suitable process. In one embodiment, the metal conductive layer 206 may include, but not limited to, Ti, Ni, Ag, Al, Al/Cu alloy, Al/Si/Cu alloy or combinations thereof. In one embodiment, the metal conductive layer 206 is formed with a thickness ranged from about 0.3 μm to about 0.5 μm, for example, about 0.3 μm, about 0.4 μm or about 0.5 μm.

Figure 5:
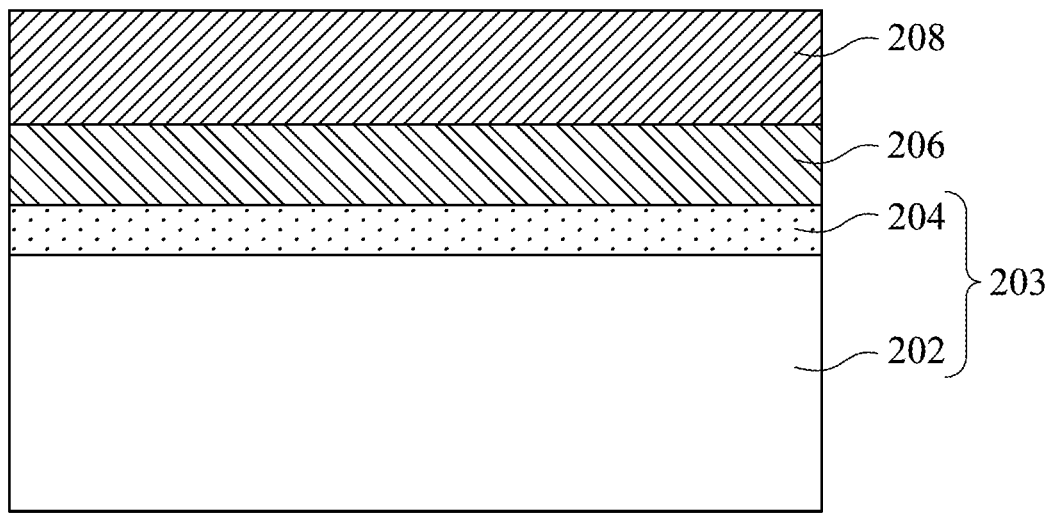

Referring to FIG. 5, in this step, an electrically conductive layer 208 is deposited over the metal conductive layer 206. In some embodiments, the electrically conductive layer 208 may be formed using PVD, CVD, electron beam evaporation, sputtering, electroplating and/or other suitable process. In some embodiments, the electrically conductive layer 208 may include, but not limited to, Ta, TaN, Cu, Ti, TiN, W or combinations thereof. In some embodiments, the electrically conductive layer 208 may have a thickness ranged from about 0.05 µm to about 0.6 µm, for example, about 0.05 µm, about 0.1 µm, about 0.2 µm, about 0.3 µm or about 0.4 µm.

Figure 6:
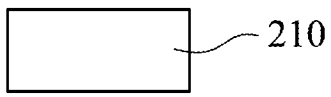
Figure 6:
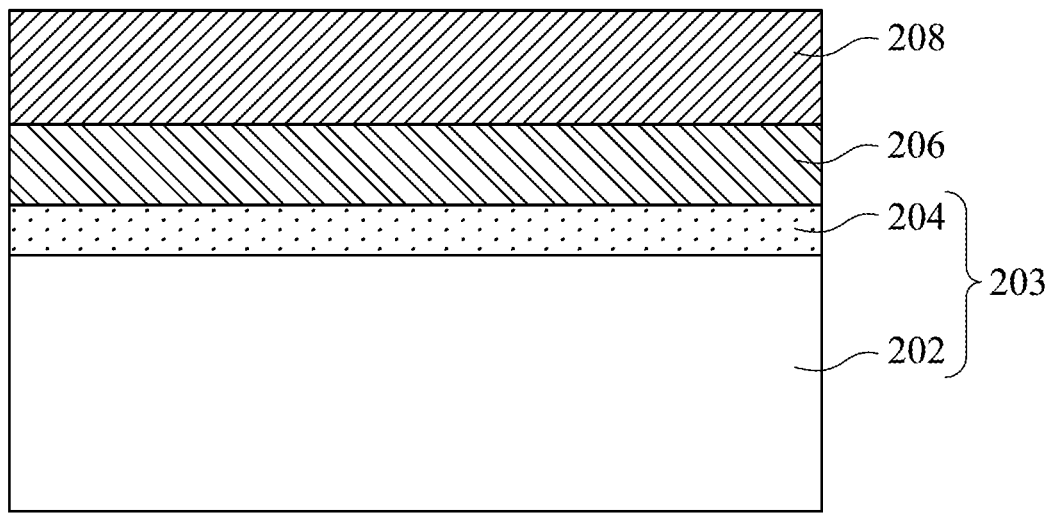
Figure 7:
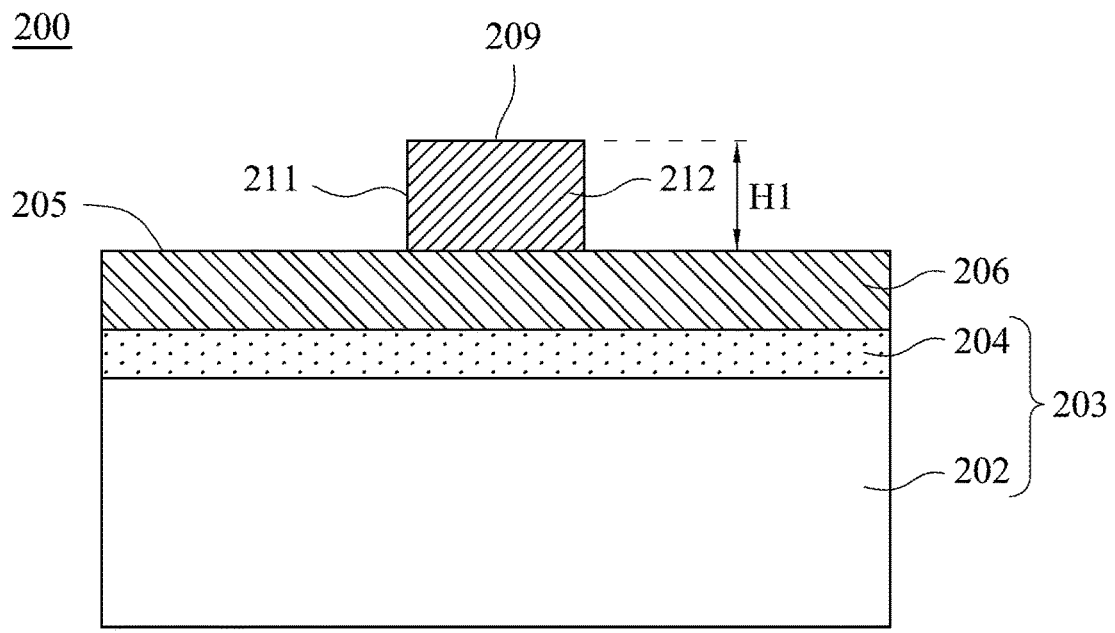

Referring to FIG. 6 and FIG. 7, a patterning process is performed on the electrically conductive layer 208, thereby forming a plurality of working electrodes 212 (only a single working electrode is shown exemplarily). As shown in FIG. 6, a patterned photoresist layer (not shown) is formed on the electrically conductive layer 208 by using a photomask 210 in a photolithographic process, and the photoresist layer may be positive photoresist or negative photoresist. Next, in FIG. 7, an etching process is performed on the electrically conductive layer 208 upon which the patterned photoresist layer is utilized, thereby forming a plurality of working electrode 212 and exposing an upper surface 205 of the metal conductive layer 206. Each working electrode 212 has a first height H1. Each working electrode 212 has a top surface 209 and a sidewall 211. Each top surface 209 is higher than the upper surface 205 of the metal conductive layer 206. Each sidewall 211 adjoins each top surface 209.

Figure 8:
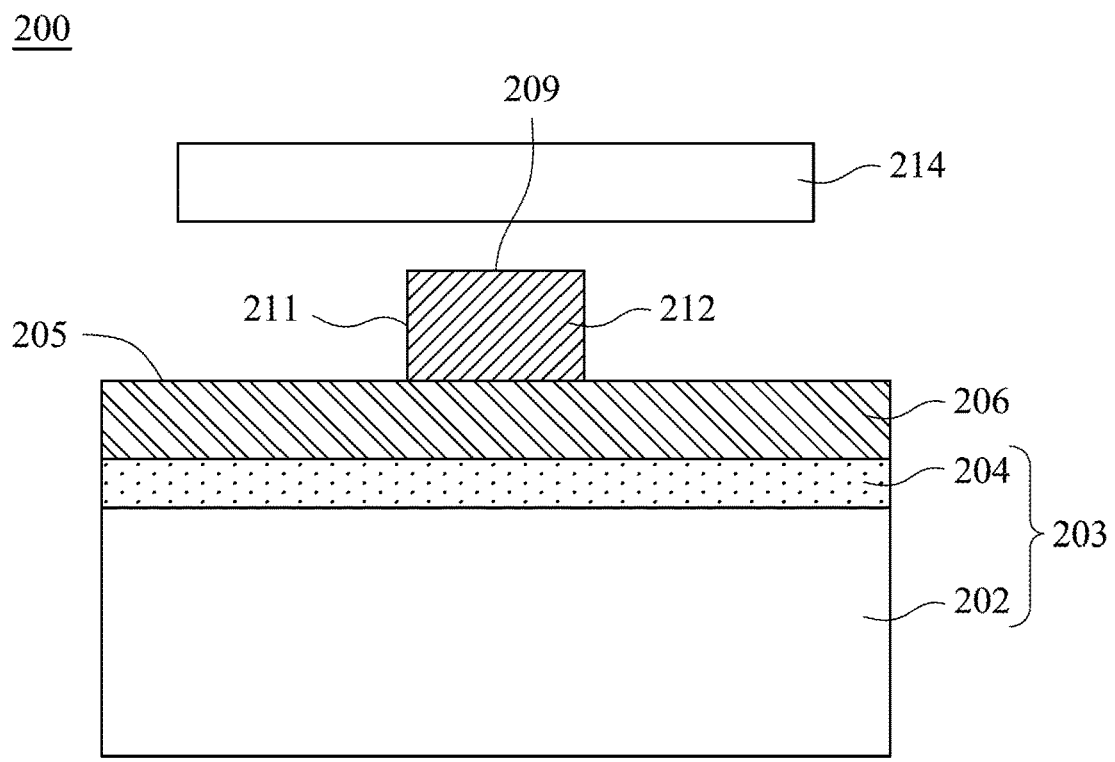
Figure 9:
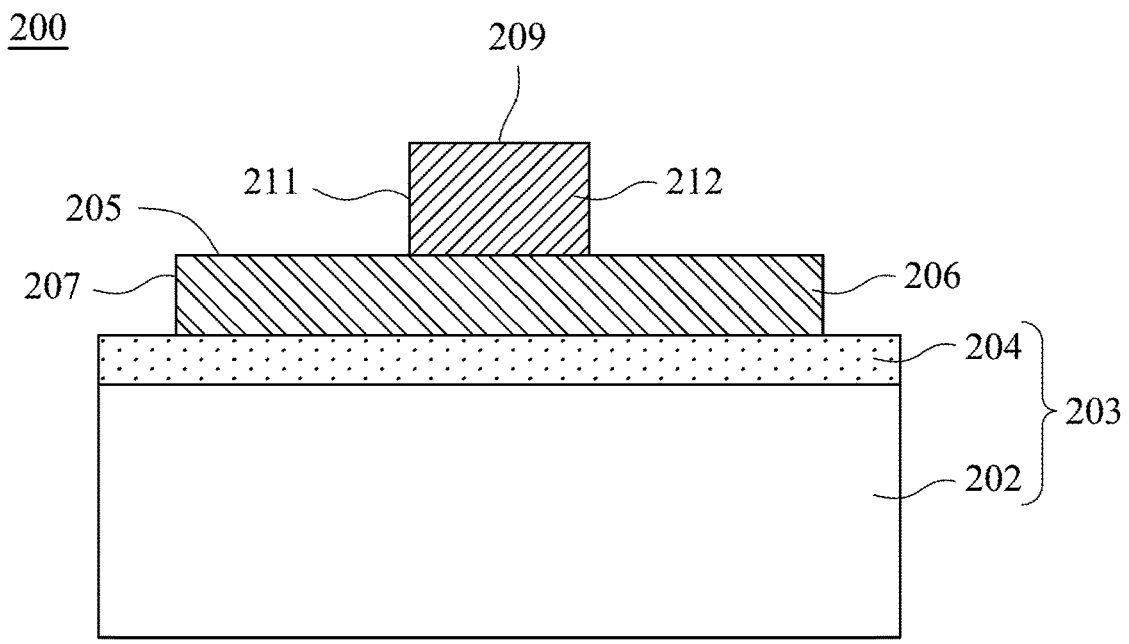

Referring to FIG. 8 and FIG. 9, a patterning process is performed on the metal conductive layer 206. As shown in FIG. 8, a patterned photoresist layer (not shown) is formed on the working electrodes 212 and the metal conductive layer 206 by using a photomask 214 in a photolithographic process, and the photoresist layer may include a positive photoresist or a negative photoresist. Next in FIG. 9, an etching process is performed on the metal conductive layer 206 upon which the patterned photoresist layer is utilized, thereby exposing a portion of an upper surface of the first insulating layer 204 below. Therefore, the metal conductive layer 206 has a sidewall 207 adjoins the upper surface 205 and the exposed portion of the upper surface of the first insulating layer 204.

Figure 10:
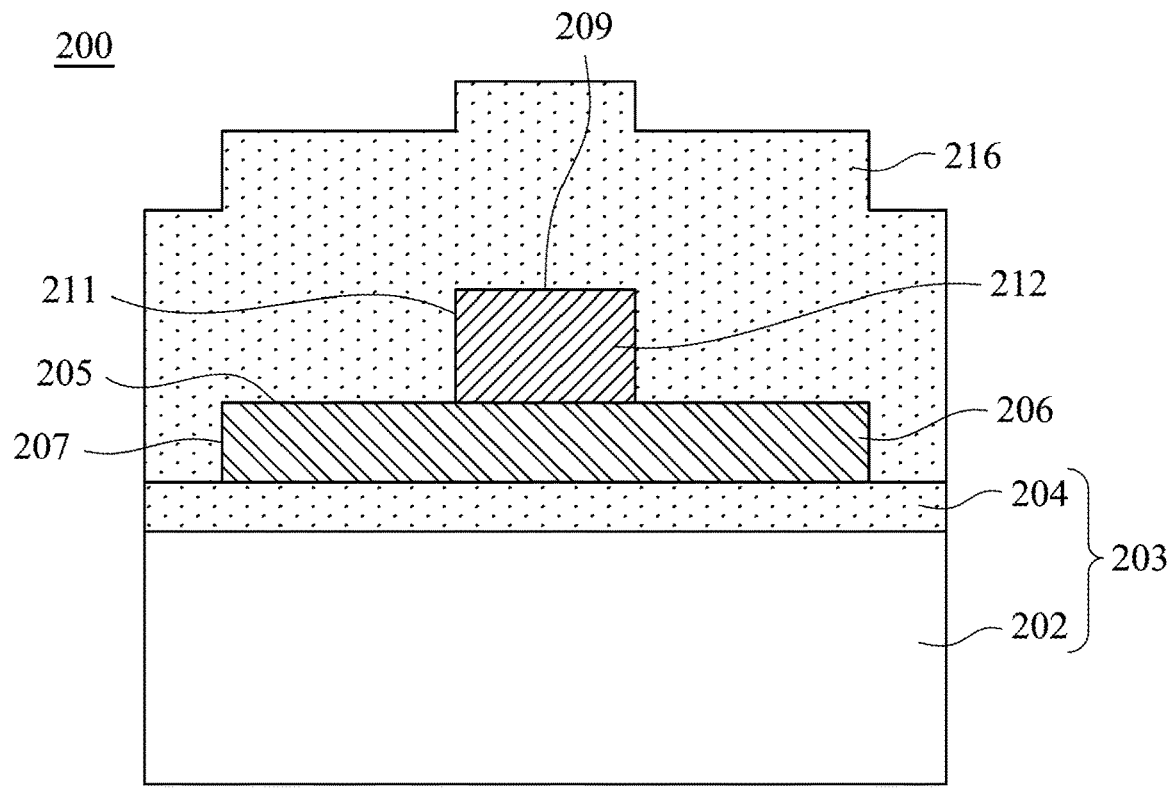

Referring to FIG. 10, an insulating material layer 216 is deposited over the first insulating layer 204, the metal conductive layer 206 and the working electrodes 212. In this step, the insulating material layer 216 may conformally cover the first insulating layer 204, the metal conductive layer 206 and the working electrodes 212. In some embodiments, the insulating material layer 216 may have multiple sub-layers and the material of each sub-layer is different from one another. In yet some embodiments, the insulating material layer 216 may have multiple sub-layers and the material of each sub-layer is the same as one another. In some embodiments, the insulating material layer 216 may be formed using PVD, CVD, plasma enhanced CVD (PECVD) and/or other suitable process.

In one embodiment, the insulating material layer 216 may include, but not limited to, an oxide, a nitride, an oxynitride or combinations thereof, such as silicon oxide, silicon nitride, and silicon oxynitride. In one embodiment, the insulating material layer 216 is made of tetraethoxysilane (TEOS).

Figure 11:
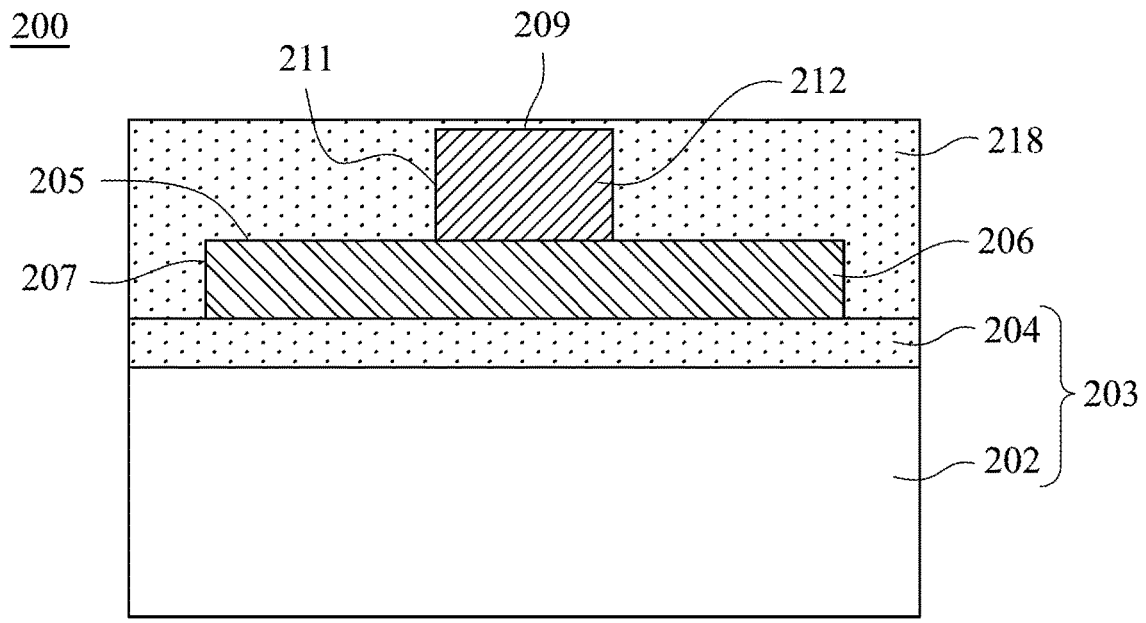

Referring to FIG. 11, a planarization process is performed on the insulating material layer 216 to form the second insulating layer 218. In this step, the planarization process is performed on the insulating material layer 216 such that the second insulating layer 218 has a substantial flat upper surface. In one embodiment, the planarization process may include chemical mechanical planarization (CMP) and/or other suitable process. In some embodiments, the insulating material layer 216 may have multiple sub-layers and the material of each sub-layer is different from one another such that the planarization process is more efficient.

Figure 12:
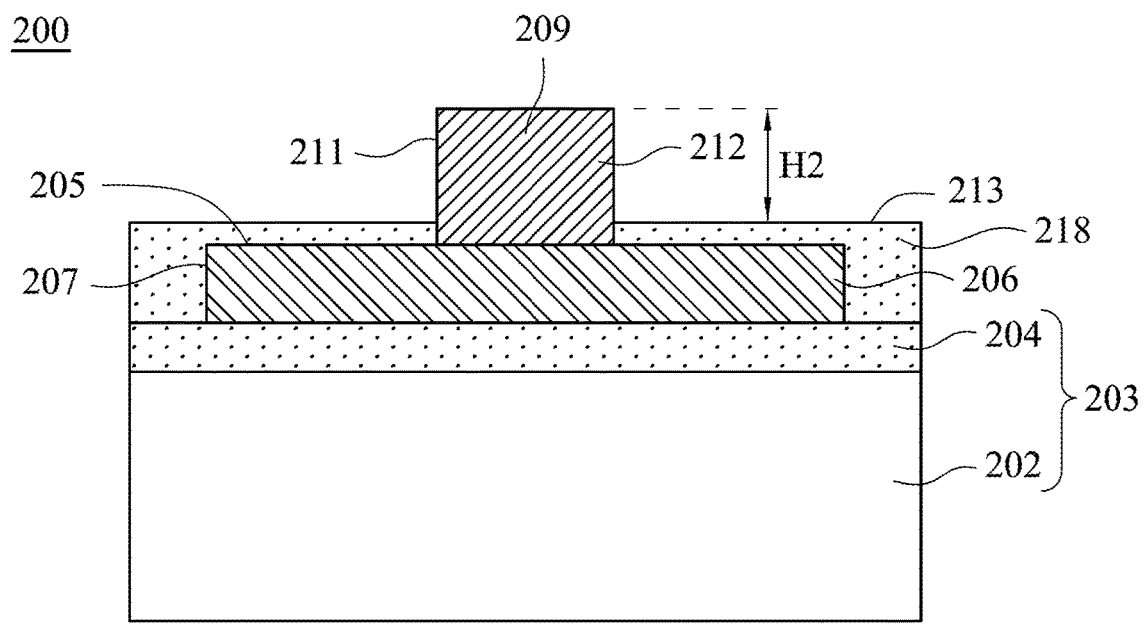

Referring to FIG. 12, a portion of the second insulating layer 218 is removed by using a suitable etching process such that an upper surface 213 of the second insulating layer 218 is positioned between the upper surface 205 of the metal conductive layer 206 and the top surfaces 209 of the working electrodes 212. Therefore, the working electrodes 212 protrude beyond the upper surface 213 of the second insulating layer 218, and the protruding portion has a second height H2 which is the vertical distance from the top surface 209 to the upper surface 213 of second isolating layer 218. In some embodiments, the second height H2 may be in a range from about 0.01 µm to about 0.5 µm, for example, about 0.05 µm, about 0.15 µm, about 0.3 µm or about 0.45 µm. In some embodiments, a plurality of biological probes may further be modified onto the working electrodes 212 such that the biological probes are connected to the top surfaces 209 of the working electrodes 212.

Figure 13:
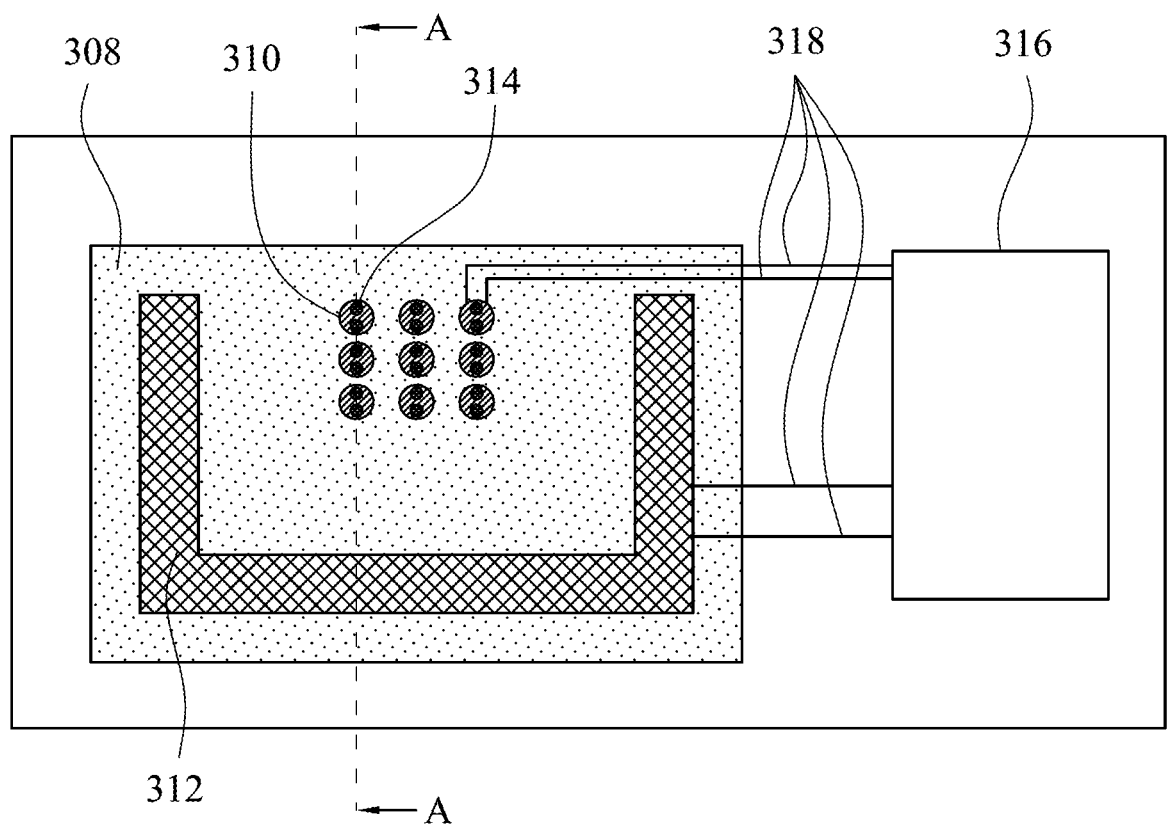
FIG. 13 is a top view of a biosensor apparatus according to some embodiments of the present disclosure.
Figure 14A:
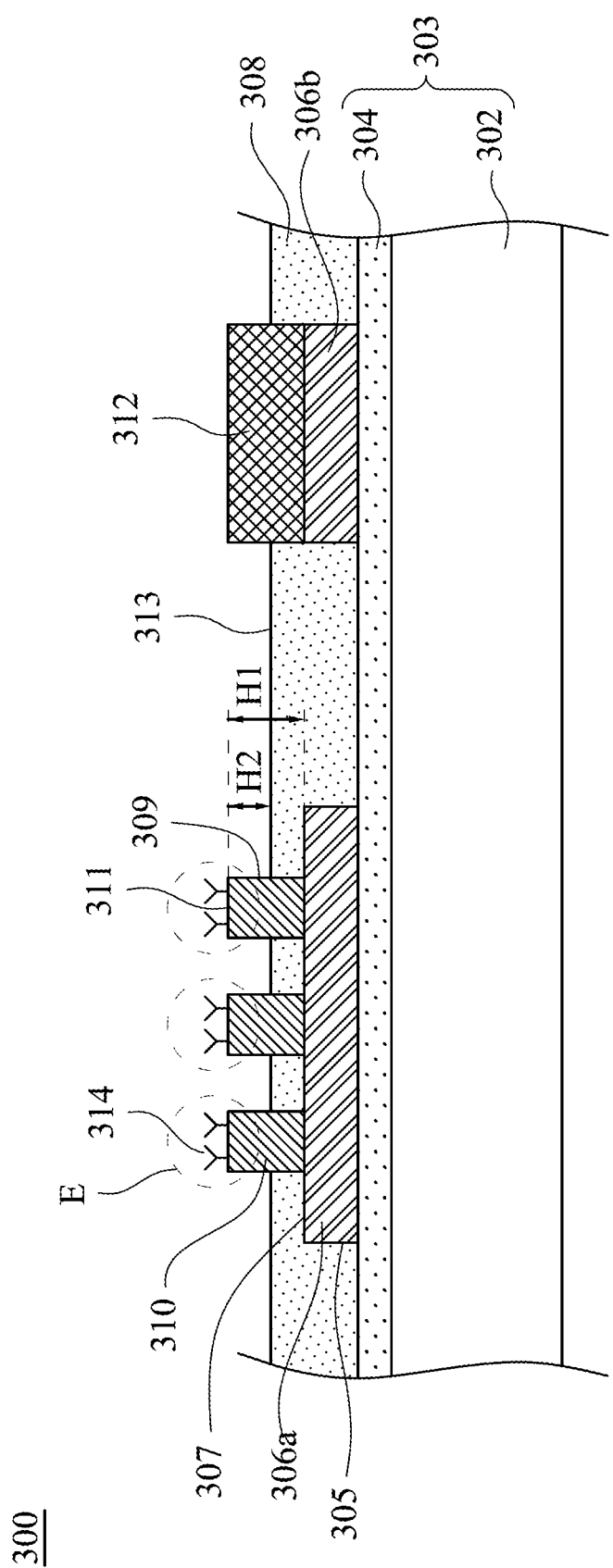
FIG. 14A is a cross-sectional view along line A-A of the biosensor apparatus according to some embodiments of the present disclosure.

The biosensor device manufactured in accordance with various embodiments of the present disclosure is compatible with various biosensor apparatuses. FIG. 13 is a top view of a biosensor apparatus in accordance with some embodiments of the present disclosure. FIG. 14A is a cross-sectional view taken along line A-A in FIG. 13. As shown in FIG. 13 and FIG. 14A, a biosensor apparatus 300 includes a substrate plate 303, a metal conductive layer 306a, a metal conductive layer 306b, a second insulating layer 308, a plurality of working electrode 310, a counter electrode 312, a plurality of biological probes 314, a signal measurement unit 316 and wires 318.

Each of the working electrodes 310 and the counter electrode 312 may be electrically connected to the signal measurement unit 316 via one or more wires 318. Therefore, as shown in FIG. 14A, when a voltage is applied to the working electrodes 310, each of the working electrodes 310 generates an electric field E surrounding the corresponding working electrode 310. In the meantime, a test sample is provided and in contact with the biological probes 314. If a target molecule in the test sample is bound to the biological probe 314, the working electrodes 310 generate a signal such that the generated signal is transmitted to the signal measurement unit 316, thereby detecting the presence of the target molecules.

Referring to FIG. 14A, the metal conductive layer 306b is disposed over the first insulating layer 304. The counter electrode 312 is disposed over the metal conductive layer 306b. In some embodiments, the material of the metal conductive layer 306b is the same as the material of the metal conductive layer 306a. In some embodiments, the material of the metal conductive layer 306b is different from the material of the metal conductive layer 306a. The substrate plate 303, the metal conductive layer 306a, the second insulating layer 308, the working electrodes 310 and the biological probes 314 may be respectively the same as the substrate plate 103, metal conductive layer 106, the second insulating layer 108, the working electrodes 110 and the biological probes 112 described hereinbefore, and the descriptions thereof are omitted to avoid repetition.

Figure 14B:
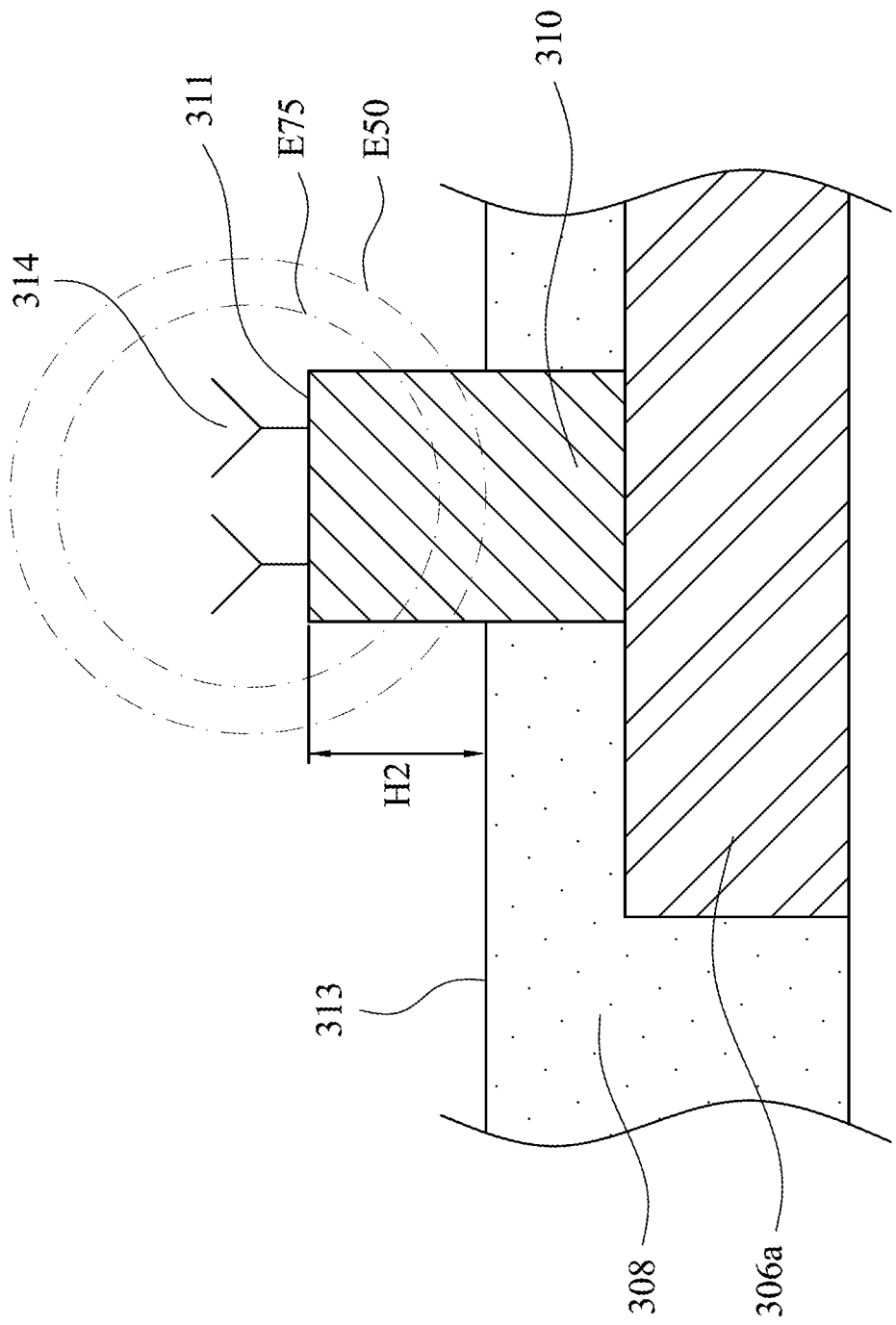
FIG. 14B is a partial magnified view exemplarily according to the cross-sectional view of FIG. 14A.

Referring to FIG. 14B, FIG. 14B is a partial magnified view exemplarily showing the cross-sectional view of FIG. 14A. When the voltage is applied to the working electrodes 310, each of the working electrodes 310 generates a corresponding electric field. Exemplarily, the dotted line E75 represents an iso-electric-field-intensity curve where the electric field intensity is 75% of the maximal electric field intensity in space. In other words, the electric field intensity of each point "inside" the dotted line E75 is greater than 75% of the maximal electric field intensity. Exemplarily, the dotted line E50 represents an iso-electric-field-intensity curve where the electric field intensity is 50% of the maximal electric field intensity in space. In other words, the electric field intensity of each point "inside" the dotted line E50 is greater than 55% of the maximal electric field intensity. In some embodiments, when a voltage is applied to the working electrodes 310, 75% of the maximum electric field intensity (i.e., the maximal magnitude of the electric field multiplied by 0.75) occurs at about 27-40% of the second height H2 from the top surfaces 311 downwardly (i.e., the intersection of the working electrodes 310 and the dotted line E75); in other words, 75% of the maximal electric field intensity occurs at about 60-73% of the second height H2 from the upper surface 313 upwardly. In some embodiments, when a voltage is applied to the working electrodes 310, 50% of the maximal electric field intensity (i.e., the maximal magnitude of the electric field multiplied by 0.5) occurs at about 80-93% of the second height H2 from the top surfaces 311 downwardly (i.e., the intersection of the working electrodes 310 and the dotted line E50); in other words, 50% of the maximal electric field intensity occurs at about 7-20% of the second height H2 from the upper surface 313 upwardly.

Simulation of Electric Field

In this experiment, COMSOL Multiphysics 4.4 simulation software was used to simulate the electric field intensity. As shown in Table 1 below, the used working electrode is in a shape of a cylinder and the cylindrical working electrode in Embodiment 1 has a radius of 0.05 μm, the maximal electric field intensity is 2.86×10$^6$ (v/m); the cylindrical working electrode in Embodiment 2 has a radius of 0.1 μm, and the maximal electric field intensity is 1.85×10$^6$ (v/m); the cylindrical working electrode in Embodiment 3 has a radius of 0.2 μm, and the maximal electric field intensity is 7.75×10$^5$ (v/m).

TABLE 1

| Working electrode | Electrode radius (μm) | Maximum magnitude of electric field (v/m) |
|---|---|---|
| Embodiment 1 | 0.05 | 2.86 × 10$^6$ |
| Embodiment 2 | 0.1 | 1.85 × 10$^6$ |
| Embodiment 3 | 0.2 | 7.75 × 10$^5$ |

As described above, the maximum magnitude of the electric field increases as electrode radius decreases. Next, as shown in Table 2 below, the coverage and the intensity of the electric field generated by the protruding part of the working electrode were simulated. When the working electrode is a conventional planar working electrode, it has a height of 0 μm (i.e., without any sidewall), and all the 100%, 75% and 50% of maximum magnitudes of the electric field occur at the level of the surface of working electrode. Then also referring to Table 2 below, calculated from the top surface of working electrode toward the insulating layer below, when the working electrode has a second height H2 of 0.15 μm, 75% of the maximal electric field intensity occurs at 0.05 μm from the top surface of working electrode; and 50% of the maximal electric field intensity occurs at 0.13 μm from the top surface of working electrode.

TABLE 2

| Height of working electrode (μm) | Height of 100% maximum magnitude of electric field | Height of 75% maximum magnitude of electric field | Height of 50% maximum magnitude of electric field |
|---|---|---|---|
| 0 | 0 | 0 | 0 |
| 0.15 | 0 | 0.05 | 0.13 |

To sum up, the biosensor device has the working electrode protruding beyond the insulating layer in accordance with various embodiments of the present disclosure. In electrochemical reactions, the greater the electric field, the faster the motion of the charged object is. As a result, the current density is higher.

A known equation of electrochemical reaction (Electrochemical Methods: Fundamentals and Applications. Allen J. Bard, Larry R. Faulkner, Wiley. ISBN: 0471043729) is shown as follows:

$$J_A(x, t) = -\left(\frac{F}{RT}\right) z_A D_A C_A(x, t) \mathscr{E}(x)$$

$J_A(x, t)$ represents a current density of a charged object A located at a site "x" in a time "t". $Z_A$ represents a valence number of the charged object A. $D_A$ represents a diffusion coefficient of the charged object A. $C_A(x, t)$ represents a concentration of the charged object A located at the site x in the time t. $\varepsilon(x)$ represents an electric field of the charged object A located at the site x. The protruding working electrode results in the wider coverage of the electric field that affects the motion of the charge object, which is conducive to enhancing the efficiency of electrochemical reaction, thereby increasing the strength of signal. Therefore, the working electrode manufactured in accordance with the embodiment of the present disclosure may have a smaller width than the width of planar electrode known in the art, thereby enhancing the sensitivity.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for manufacturing a biosensor device, comprising the step of:
   providing a substrate plate;
   forming a metal conductive layer over the substrate plate, and the metal conductive layer having an upper surface;
   forming a plurality of working electrodes over the upper surface of the metal conductive layer, wherein each of the working electrodes has a top surface that is higher than the upper surface of the metal conductive layer, wherein the working electrodes is selected from the group consisting of Ta, TaN, Cu, Ti, TiN, W, Ni, Ag, Al, Al/Cu alloy, Al/Si/Cu alloy and combinations thereof, wherein each of the working electrodes has a first height protruding beyond the metal conductive layer, and the first height ranges from about 0.05 μm to about 0.6 μm, wherein each of the working electrodes has an aspect ratio ranged from about 0.125 to about 2.5; and
   forming an insulating layer covering the metal conductive layer and surrounding the working electrodes, wherein an upper surface of the insulating layer is between the top surfaces of the working electrodes and the upper surface of the metal conductive layer so that the working electrodes protrude beyond the upper surface of the insulating layer, wherein each of the working electrodes protrude from the upper surface a second height, and the second height is about 0.01 µm to about 0.5 µm.

2. The method of claim 1, wherein the step of forming the working electrodes comprises:
    depositing an electrically conductive layer over the upper surface of the metal conductive layer; and
    patterning the electrically conductive layer to form the working electrodes.

3. The method of claim 1, wherein the step of forming the insulating layer comprises:
    depositing an insulating material layer over the metal conductive layer and the working electrodes;
    performing a planarization process on the insulating material layer to form a planarized insulating material layer; and
    etching the planarized insulating material layer to form the insulating layer.

4. The method of claim 1, wherein each of the working electrodes further comprises a sidewall adjoining the top surface, and the insulating layer covers a portion of each of the sidewalls.

5. The method of claim 1, wherein the working electrodes are in a shape of a cylinder, a triangular prism, a quadrangular prism, a pentagonal prism, a hexagonal prism or an octagonal prism.

6. The method of claim 1, further comprising connecting a plurality of biological probes to the working electrodes, wherein the biological probes are nucleic acid, cell, antibody, enzyme, polypeptide or combinations thereof.

7. A biosensor device, comprising:
    a substrate plate;
    a metal conductive layer disposed over the substrate plate and the metal conductive layer having an upper surface;
    a plurality of working electrodes disposed over the upper surface of the metal conductive layer, wherein each of the working electrodes has a top surface that is higher than the upper surface of the metal conductive layer, wherein the working electrodes is selected from the group consisting of Ta, TaN, Cu, Ti, TiN, W, Ni, Ag, Al, Al/Cu alloy, Al/Si/Cu alloy and combinations thereof, wherein each of the working electrodes has a first height protruding beyond the metal conductive layer, and the first height ranges from about 0.05 µm to about 0.6 µm, wherein each of the working electrodes has an aspect ratio ranged from about 0.125 to about 2.5; and
    an insulating layer covering the metal conductive layer and surrounding the working electrodes, wherein an upper surface of the insulating layer is between the top surfaces of the working electrodes and the upper surface of the metal conductive layer, so that the working electrodes protrude from the upper surface of the insulating layer a second height, wherein each of the working electrodes protrudes from the upper surface a second height, and the second height is about 0.01 µm to about 0.5 µm.

8. The biosensor device of claim 7, wherein the metal conductive layer further comprises a sidewall adjoining the upper surface of the metal conductive layer, and the insulating layer covers the sidewall of the metal conductive layer.

9. The biosensor device of claim 7, wherein each of the working electrodes further comprises a sidewall adjoining the top surface, and the insulating layer covers a portion of each of the sidewalls.

10. The biosensor device of claim 7, wherein the working electrodes are in a shape of a cylinder, a triangular prism, a quadrangular prism, a pentagonal prism, a hexagonal prism or an octagonal prism.

11. The biosensor device of claim 7, further comprising a plurality of biological probes connected to the working electrodes, wherein the biological probes are nucleic acid, cell, antibody, enzyme, polypeptide or combinations thereof.

12. A method for detecting biological molecules, comprising:
    providing a sample comprising a target molecule;
    providing the biosensor device of claim 7;
    connecting a plurality of biological probes to the working electrodes;
    applying a voltage to the working electrodes such that the working electrodes generate an electric field surrounding the working electrodes; and
    contacting the sample with the biological probes such that the target molecule in the sample is bound to the biological probes, thereby generating a signal from the working electrodes.

13. The method of claim 12, wherein the step of applying the voltage to the working electrodes comprises: applying a voltage to the working electrodes such that 75% of the maximal electric field intensity occurs at about 27% to about 40% of the second height from the top surfaces toward the upper surface of the insulating layer.

14. The method of claim 12, wherein the step of applying the voltage to the working electrodes comprises: applying a voltage to the working electrodes such that 50% of the maximal electric field intensity occurs at about 80% to about 93% of the second height from the top surfaces toward the upper surface of the insulating layer.

* * * * *